US010531787B2

(12) United States Patent
Dillon et al.

(10) Patent No.: US 10,531,787 B2
(45) Date of Patent: Jan. 14, 2020

(54) STEERABLE MULTILUMEN CATHETER SHAFT

(71) Applicant: Cook Medical Technologies, Bloomington, IN (US)

(72) Inventors: Travis E. Dillon, Winston-Salem, NC (US); Michael Lee Williams, Pinnacle, NC (US); Kenneth C. Kennedy, II, Clemmons, NC (US); Ronan T. Young, Spencer, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 183 days.

(21) Appl. No.: 15/655,239

(22) Filed: Jul. 20, 2017

(65) Prior Publication Data
US 2018/0028778 A1 Feb. 1, 2018

Related U.S. Application Data

(60) Provisional application No. 62/367,910, filed on Jul. 28, 2016, provisional application No. 62/367,918, (Continued)

(51) Int. Cl.
A61B 1/005 (2006.01)
A61M 25/01 (2006.01)
A61M 25/00 (2006.01)

(52) U.S. Cl.
CPC .......... A61B 1/0051 (2013.01); A61B 1/0052 (2013.01); A61B 1/0057 (2013.01);
(Continued)

(58) Field of Classification Search
CPC ............ A61M 25/005; A61M 25/0052; A61M 25/0053; A61M 25/0054; A61M 25/0141;
(Continued)

(56) References Cited

U.S. PATENT DOCUMENTS 3,470,876 A * 10/1969 Barchilon ............ A61B 1/0052
138/120
3,681,164 A 8/1972 Bazinet, Jr. et al.
(Continued)

FOREIGN PATENT DOCUMENTS

FR 2723527 2/1996
WO WO 2010/075245 A2 7/2010

OTHER PUBLICATIONS

International Search Report and Written Opinion, dated Nov. 10, 2017, for International Application No. PCT/US2017/042989.

Primary Examiner — Kami A Bosworth
(74) Attorney, Agent, or Firm — Brinks Gilson & Lione

(57) ABSTRACT

A multilumen catheter shaft body includes a proximal end segment with a first durometer and a first longitudinal length dimension. A proximal intermediate segment is fixedly joined to a distal end of the proximal end segment and includes a second durometer and a second longitudinal length dimension. A distal intermediate segment is fixedly joined to a distal end of the proximal intermediate segment and includes a third durometer and a third longitudinal length dimension. A distal terminal end segment is fixedly joined to a distal end of the distal intermediate segment and includes a fourth durometer and a fourth longitudinal length dimension. The first durometer is greater than at least the second and third durometers. The fourth durometer is greater than at least the second and third durometers. A plurality of parallel longitudinal lumens extends through the body, providing a structure useful in a cholangioscope or other endoscopic applications.

18 Claims, 5 Drawing Sheets

Related U.S. Application Data filed on Jul. 28, 2016, provisional application No. 62/367,938, filed on Jul. 28, 2016, provisional application No. 62/367,959, filed on Jul. 28, 2016.

(52) U.S. Cl.
CPC .... *A61M 25/0026* (2013.01); *A61M 25/0028* (2013.01); *A61M 25/0105* (2013.01); *A61M 25/0136* (2013.01); *A61M 25/0147* (2013.01); *A61M 2025/004* (2013.01)

(58) Field of Classification Search
CPC ...... A61M 25/0147; A61M 2025/0036; A61M 2025/015; A61B 1/0057
See application file for complete search history.

(56) References Cited

U.S. PATENT DOCUMENTS

| | | | |
|---|---|---|---|
| 4,407,273 A | 10/1983 | Ouchi | |
| 4,648,892 A | 3/1987 | Kittrell et al. | |
| 4,784,144 A | 11/1988 | Ono et al. | |
| 4,790,295 A | 12/1988 | Tashiro | |
| 4,813,400 A | 3/1989 | Washizuka et al. | |
| 4,899,732 A | 2/1990 | Cohen | |
| 4,904,048 A | 2/1990 | Sogawa et al. | |
| 4,911,148 A | 3/1990 | Sosnowski et al. | |
| 4,984,563 A | 1/1991 | Renaud | |
| 4,991,957 A | 2/1991 | Sakamoto et al. | |
| 5,169,568 A | 12/1992 | Ainger, III | |
| 5,199,417 A | 4/1993 | Muller et al. | |
| 5,370,108 A | 12/1994 | Miura et al. | |
| 5,399,164 A * | 3/1995 | Snoke | A61M 25/01 604/264 |
| 5,463,712 A | 10/1995 | Cawood | |
| 5,665,051 A | 9/1997 | Quick et al. | |
| 5,851,464 A * | 12/1998 | Davila | A61M 25/001 264/103 |
| 5,885,209 A * | 3/1999 | Green | A61B 1/0011 600/104 |
| 6,585,718 B2 | 7/2003 | Hayzelden et al. | |
| 7,502,537 B2 | 3/2009 | Kurahashi | |
| 7,618,177 B2 | 11/2009 | Cazzini | |
| 7,922,650 B2 | 4/2011 | McWeeney et al. | |
| 7,922,654 B2 | 4/2011 | Boutillette et al. | |
| 8,608,649 B2 | 12/2013 | McWeeney et al. | |
| 8,725,228 B2 | 5/2014 | Koblish et al. | |
| 9,215,970 B2 | 12/2015 | Boutillette et al. | |
| 9,307,893 B2 | 4/2016 | Kennedy, II et al. | |
| 2002/0087049 A1* | 7/2002 | Brock | A61B 17/0469 600/114 |
| 2002/0198492 A1 | 12/2002 | Miller et al. | |
| 2003/0114832 A1* | 6/2003 | Kohler | A61B 17/00234 604/528 |
| 2004/0042745 A1 | 3/2004 | Nakatate et al. | |
| 2004/0243102 A1* | 12/2004 | Berg | A61M 25/0013 604/525 |
| 2005/0197623 A1* | 9/2005 | Leeflang | A61M 25/0144 604/95.04 |
| 2006/0245702 A1 | 11/2006 | Cazzini | |
| 2007/0060997 A1 | 3/2007 | de Boer | |
| 2010/0206453 A1* | 8/2010 | Leeflang | A61M 25/0009 156/60 |
| 2012/0209073 A1 | 8/2012 | McWeeney et al. | |
| 2013/0172673 A1 | 7/2013 | Kennedy, II et al. | |
| 2013/0172677 A1 | 7/2013 | Kennedy, II et al. | |
| 2013/0172678 A1 | 7/2013 | Kennedy, II et al. | |
| 2014/0046129 A1 | 2/2014 | Boutillette et al. | |
| 2014/0303599 A1 | 10/2014 | Heideman et al. | |
| 2014/0309661 A1* | 10/2014 | Sheps | A61M 25/0147 606/130 |
| 2015/0057537 A1 | 2/2015 | Dillon et al. | |
| 2015/0272734 A1 | 10/2015 | Sheps et al. | |
| 2015/0352327 A1 | 12/2015 | Helgeson et al. | |

\* cited by examiner

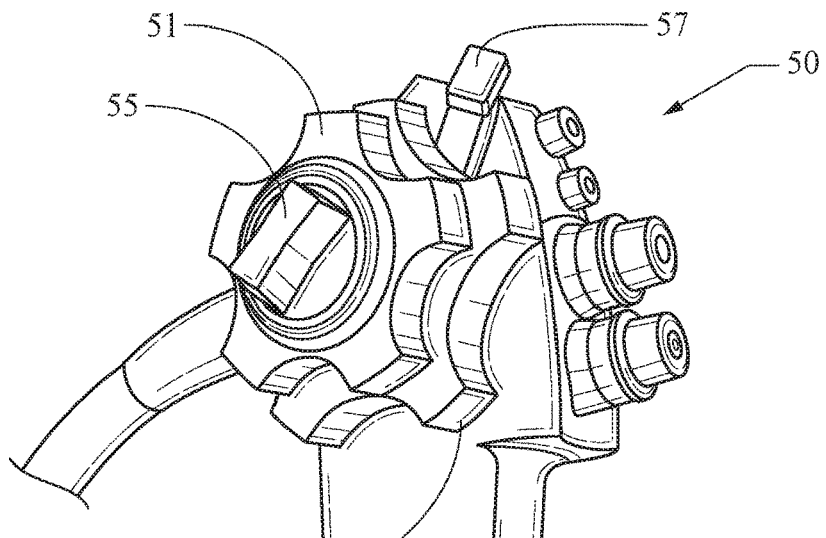
FIG. 1
(Prior Art)
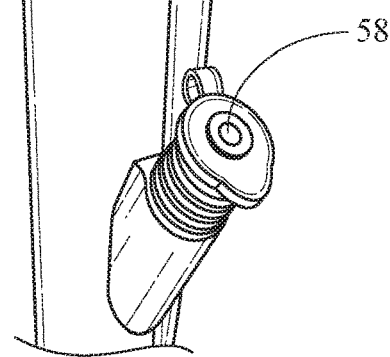
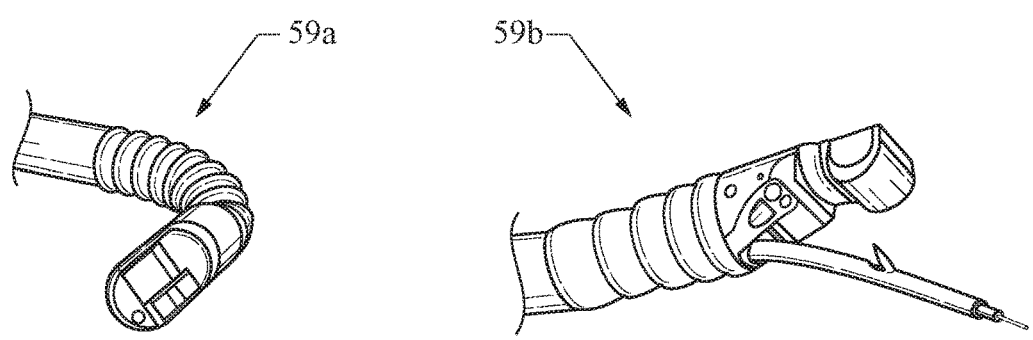
FIG. 1A
(Prior Art)
FIG. 1B
(Prior Art)

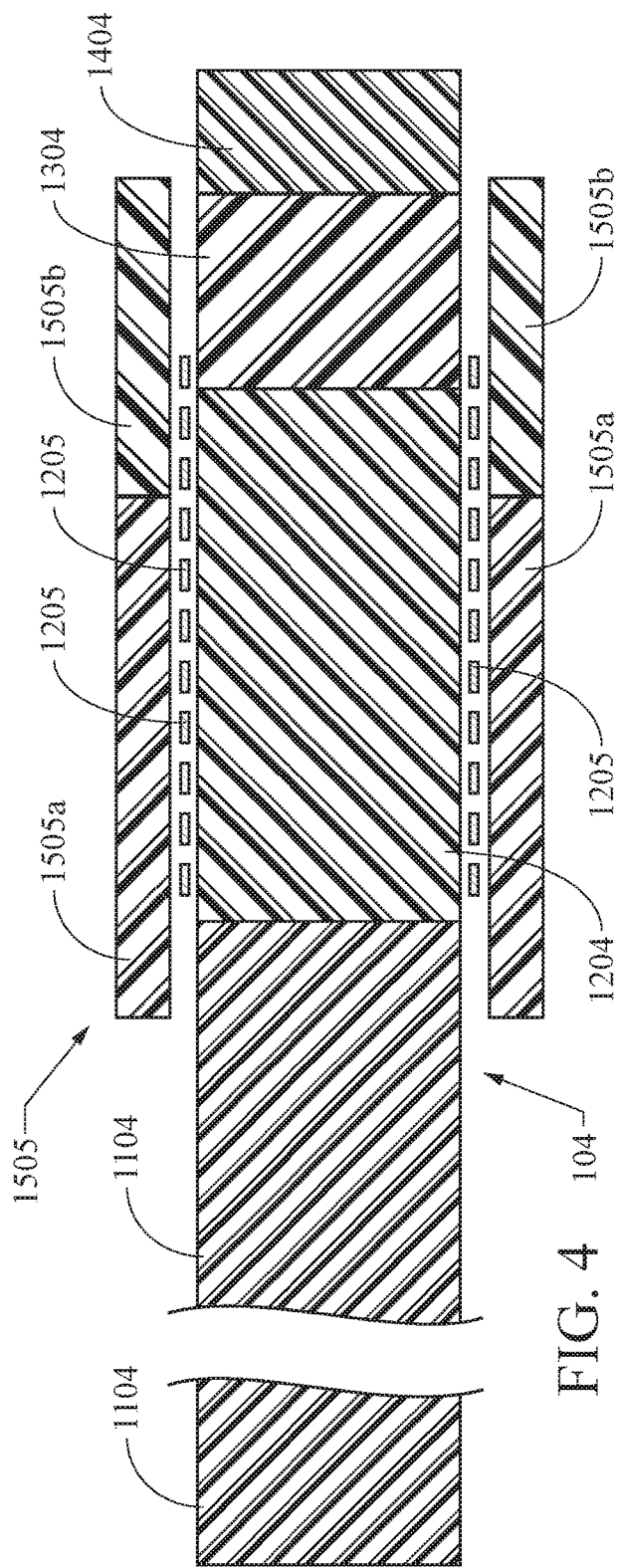
FIG. 4
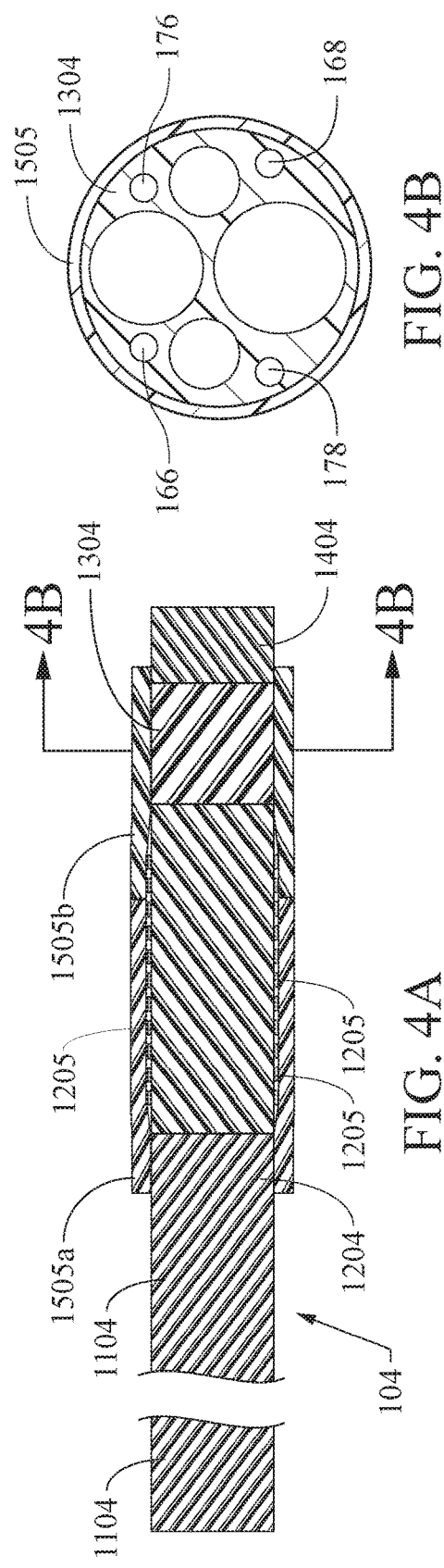
FIG. 4A
FIG. 4B

STEERABLE MULTILUMEN CATHETER SHAFT

CROSS-REFERENCE TO RELATED APPLICATIONS

This application is a non-provisional application which claims priority to U.S. provisional application Ser. Nos. 62/367,910; 62/367,918; 62/367,938; and 62/367,959; all filed Jul. 28, 2016, each of which is incorporated by reference herein in its entirety.

TECHNICAL FIELD

Embodiments disclosed herein generally relate to steerable medical catheter devices, including endoscopes. More particularly embodiments disclosed herein relate to a structures and methods for a shaft of a steerable small-diameter catheter.

BACKGROUND

Deflecting catheters, also referred to as steerable catheters are used in a variety of medical and non-medical procedures. In diagnostic and therapeutic medical procedures, a steerable catheter provides an operator (e.g., physician) with the ability to articulate the distal tip of the catheter in order to travel through constrained and/or tortuous anatomy, and/or to direct the distal catheter tip in a particular direction. Similar mechanisms are used in medical and nonmedical endoscopes to steer them to a target site and to orient a device portion (e.g., including a camera or other visualization means) in a desired direction.

In a typical design, control wires are manipulably attached at a proximal end of the device, and also attached at or near a distal end of the device. Such a configuration operates by manipulating one or more of the control wires to increase and/or decrease a generally longitudinal force on the distal device end that will deflect it in a desired direction. As described with reference to an existing steerable endoscopic camera device 50 of FIG. 1, the control wires may be actuated by rotation of control wheels 51, 53. Each control wheel can be rotated to operate a control wire or pair of control wires in a manner exerting push/pull tension on a deflectable distal device portion (not shown, but well-known in the art) to deflect that portion along a first plane, while the other control wheel operates similarly to deflect that portion along a second plane intersecting (e.g., orthogonal to) the first plane. At times, it is desirable to lock that distal device portion into a particular deflected orientation (e.g., so that the operator may execute another task requiring releasing hand contact with one or both control wheels). The illustrated device 50 includes a first brake for the first control wheel 51, with a twistable knob 55 for locking/unlocking an internal brake mechanism that operates along the central rotational axis of the first control wheel 51. The illustrated device 50 includes a second brake for the second control wheel 53, with a lever 57 for locking/unlocking an internal brake mechanism that operates by exerting a braking engagement along the central rotational axis of the second control wheel 53. One or both brake controls 55, 57 require a user to change his/her grip for actuation.

A variety of different steerable shaft constructions have been used in different prior catheters and endoscopes. Each shaft typically has at least one working channel that extends longitudinally therethrough (e.g., through a working channel port 58 in the handle, shown capped). A steerable catheter device may be configured as a gastrointestinal duodenoscope with a distal terminal end construction 59a as shown in FIG. 1A or as an endoscopic ultrasound (EUS) endoscope with a distal terminal end construction 59b as shown in FIG. 1B, which also shows a tool structure extending out through that scope's working channel lumen.

A variety of different steerable shaft constructions have been used in different prior catheters and endoscopes. However, there are special challenges and needs for a small-diameter catheter (e.g., less than 10 mm, less than 5 mm, or less than 4 mm and greater than 2.5 mm) configured for use through a side-viewing endoscope—such as a duodenoscope. In particular, such a device will need different resistance to crimping, kinking, and/or collapse along its length during operation and manipulation—including during introduction into and operation within a biliary tree of a human or non-human patient.

It is be desirable to provide a catheter shaft design that is configured and dimensioned for operation as a cholangioscope. Moreover, there is a need for a catheter device like this that provides economic diagnostic, therapeutic, and economic benefit to patients and caregivers by providing reliably predictable operative functionality and resistance to impaired structure or function during typical operations.

BRIEF SUMMARY

In one aspect, embodiments disclosed herein may include a multilumen catheter shaft body with a proximal end segment with a first durometer and a first longitudinal length dimension. A proximal intermediate segment is fixedly joined to a distal end of the proximal end segment and includes a second durometer and a second longitudinal length dimension. A distal intermediate segment is fixedly joined to a distal end of the proximal intermediate segment and includes a third durometer and a third longitudinal length dimension. A distal terminal end segment is fixedly joined to a distal end of the distal intermediate segment and includes a fourth durometer and a fourth longitudinal length dimension. The first durometer is greater than at least the second and third durometers. The fourth durometer is greater than at least the second and third durometers. A plurality of parallel longitudinal lumens extends through a major length, or the entire length of the body, providing a structure useful in a cholangioscope or other endoscopic applications.

In another aspect, embodiments disclosed herein may include various catheter constructions that have a plurality of greater than two discreet lengthwise sections with differing durometers, where a distal lengthwise portion includes overlying material modifying the effective overall catheter durometer/flexibility, where the core catheter body has a distalmost segment with a same or substantially same durometer as a proximal segment, and where the discreet sections are securely and permanently affixed together at end-abutting joints.

BRIEF DESCRIPTION OF THE DRAWINGS

FIG. 1 is a view of a prior art steerable/deflectable catheter device embodied as an endoscope;

FIGS. 1A and 1B show distal terminal end configurations of prior art devices like that of FIG. 1, with and through which embodiments of the present device embodiments may be used;

FIG. 4 is a diagrammatic, partially expanded/exploded view, in simplified longitudinal section, of a catheter shaft construction;

FIG. 4A shows a diagrammatic, "more-assembled" view of the catheter shaft body of FIG. 4;

FIG. 4B depicts a transverse section view of the catheter shaft body taken along line 4B-4B of FIG. 4A;

DETAILED DESCRIPTION

Figure 2:
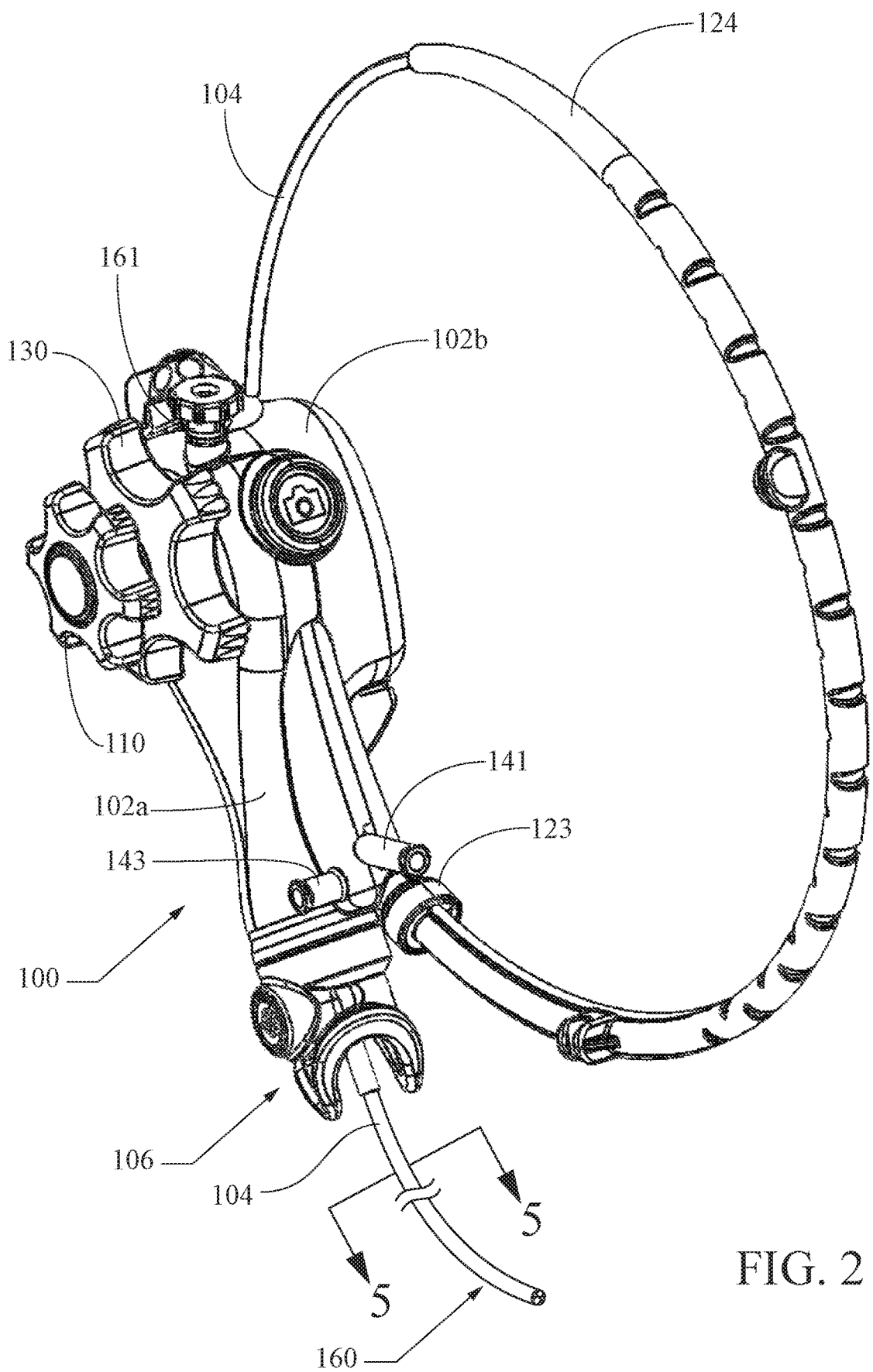
FIG. 2 depicts a perspective view of a steerable catheter device of the present disclosure.

Various embodiments are described below with reference to the drawings in which like elements generally are referred to by like numerals. The relationship and functioning of the various elements of the embodiments may better be understood by reference to the following detailed description. However, embodiments are not limited to those illustrated in the drawings. It should be understood that the drawings may be, but are not necessarily to scale, and in certain instances details may have been omitted that are not necessary for an understanding of embodiments disclosed herein, such as—for example—conventional fabrication and assembly.

The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise. Reference herein to any industry standards (e.g., ASTM, ANSI, IEEE standards) is defined as complying with the currently published standards as of the original filing date of this disclosure concerning the units, measurements, and testing criteria communicated by those standards unless expressly otherwise defined herein.

The terms "proximal" and "distal" are used herein in the common usage sense where they refer respectively to a handle/doctor-end of a device or related object and a tool/patient-end of a device or related object. The terms "about," "substantially," "generally," and other terms of degree, when used with reference to any volume, dimension, proportion, or other quantitative or qualitative value, are intended to communicate a definite and identifiable value within the standard parameters that would be understood by one of skill in the art (equivalent to a medical device engineer with experience in this field), and should be interpreted to include at least any legal equivalents, minor but functionally-insignificant variants, standard manufacturing tolerances, and including at least mathematically significant figures (although not required to be as broad as the largest range thereof).

The term "control wire" (including just "wire") is used herein to denote the elongate members that connect a control surface of a steerable catheter with a deflectable distal portion of the catheter, and it may include metallic, polymeric, and/or other materials including—by way of non-limiting example—ultrahigh molecular weight polyethylene yarn (e.g., Dyneema™), aramid fibers, monofilament line, multifilament/multifilar cable, and/or other materials that preferably have high tensile strength with low longitudinal stretch so as to provide predictable operation behavior. With regard to distal attachment of the control wire(s), a multifilar, braided, or other structure may be used, which may structure be at least partially frayed or otherwise partially disaggregated (e.g., in order to provide greater surface area than a unitary aggregated wire structure, as described further below).

One example of a control wire may include a 4x-50 Denier ultra-high tenacity polyethylene braid having a very small outer diameter of about 0.18 mm (measured in accordance with ASTM D-1907); high strength (about 5.6 kg, and at least equal to or greater than 4.75 kg, measured in accordance with ASTM D-6775); low longitudinal stretch/elongation (about 5%, ±2%, measured in accordance with ASTM D-6775) (e.g., as available from Textile Development Associates Inc. of Brookfield, Conn.). Certain preferred control wire embodiments include or may even consist of high modulus fiber material that is nonconductive and/or substantially nonstretching. In one embodiment, a high modulus fiber control wire material may be braided. One such high modulus fiber material can be a High Molecular Density Polyethylene, a melt spun liquid crystal polymer fiber rope, or a spun para-aramid fiber polymer, or a high strength ceramic fiber. In some embodiments, a high modulus fiber control wire material may have a tensile strength in a range of about 300 ksi (2,000 MPa) to 1,500 ksi (10,400 MPa), and/or a tensile modulus in the range of about 5,000 ksi (35,000 MPa) to about 20,000 ksi (140,000 MPa). Another control wire structure, useful on its own or with one or more other control wire materials, may include an optical fiber. Optical fibers are known that may be load-bearing with sufficient tensile strength to function as control wires while also having the ability to transmit light through the length of such a fiber. In certain embodiments one or more of the control wires may consist of or may comprise optical fiber that can serve both for mechanical operation and for transmitting light through the catheter shaft.

In particular, embodiments described here provide a robust but highly flexible steerable/deflectable catheter body useful for a variety of medical applications (e.g., for general steerable delivery to a target site, as a cholangioscope equipped with at least one visualization element such as an optical element, CCD, or CMOS visualization element or other camera/camera-like component). In particular, certain embodiments will have a very small outer diameter that preferably is no more than 10.5 Fr (about 3.5 mm). The overall length may be dimensioned for passage and operation through a duodenoscope or other gastrointestinal (or other) endoscope. When configured for use with a duodenoscope (see, e.g., FIG. 1A), an endmost shaft length may be configured with a flexible body that can bend at/around the duodenoscope's elevator without significant distortion of its inner lumens, and where the endmost terminal length may be configured to deflect to (or nearly to) 90° relative to the adjacent shaft length.

Embodiments of a handle are described with reference to FIGS. 2-4, where FIG. 2 shows a steerable catheter device of the present disclosure including a handle portion assembly 100 with a steerable catheter body 104 extending distally therefrom (which may have a default straight linear configuration, and for which is illustrated only a slightly-deflected distal end terminal lengthwise portion). Various embodiments may include one or more different steering control means known in the art. This illustrated embodiment includes a pair of control wheels, with an outer control wheel 110 and an inner control wheel 130. As set forth in greater detail below (including with reference to FIGS. 2-3), the outer control wheel 110 is disposed in mechanical communication with a pair of control wires that are operable, upon wheel rotation, to deflect at least the distal end portion 160 of the catheter body 104 along a first plane, and the inner control wheel 130 is disposed in mechanical communication with another pair of control wires that are operable, upon wheel rotation, to deflect the catheter body 104 along a second plane that may be generally orthogonal to the first plane, and is at least somewhat offset from that first plane. Simultaneous or sequential operation of the outer and inner wheels 110, 130 preferably will deflect the distal end portion 160 of the catheter body 104 in any direction around a 360-degree circle defined generally by a circumference of the catheter.

Steering mechanisms using control wires are well-known in the art including in U.S. Pat. Pub. No. 2015/0366435 to Williams, which is incorporated herein by reference in its entirety. The overall control structure described is also well known in the steerable device art, including particularly the endoscope art, but those devices lack the currently disclosed finely-controlled mechanism for efficient and effective tensioning of control wires. Certain embodiments in keeping with the present disclosure may include at least one visualization element (as well as supporting hardware and/or software, not shown—but well-known in the art and readily understandable as using electrical and/or optical devices such as CCD, fiber optic, CMOS, etc.) for use of such embodiments as endoscopic devices including, for example, as a cholangioscope configured for use with and through a larger endoscope. The illustrated handle embodiment 100 is configured for secure attachment to a working channel of a larger endoscope (e.g., as shown in FIG. 1), and it may include any number of different attachment/mounting mechanisms 106, such as—for example—those described and illustrated in U.S. Pat. App. Pub. No. 2015/0057537 and/or 2016/0089008, each of which is incorporated by reference herein in its entirety.

In FIG. 2, a strain-relief sheath 124 is shown attached to and extending from a near-distal catheter-base port 123 of the handle housing 102, which strain-relief sheath is described below in greater detail. A vacuum channel port member 141 and a flush port member 142 are also shown adjacent the near-distal catheter-base port 123 of the handle housing 102. A working channel port member 161 extends from a proximal end portion 161a of the handle housing 102 and provides for mechanical and fluid communication with at least one lumen of the catheter 104. The multilumen catheter body 104 extends out from a near-distal catheter-base port 123 (through a strain relief sheath 124, if present) and loops around where it can movably/removably re-enter a proximal catheter-track port 163 of the handle housing 102 (see FIG. 3).

The mounting/attachment structure may interface with and connect to a partially-illustrated larger steerable device such as an endoscope 50, where—as noted above—embodiments of the present device may be securely mounted thereto in a manner with the present catheter 104 extending into the working channel port 58. Most of the internal components are assembled between the first and second halves 102a, 102b of the handle housing 102. FIG. 3 is a partially disassembled view of a handle housing of the device of FIG. 2, showing internal structure and components of the device mounted to the housing portion 102b.

Figure 3:
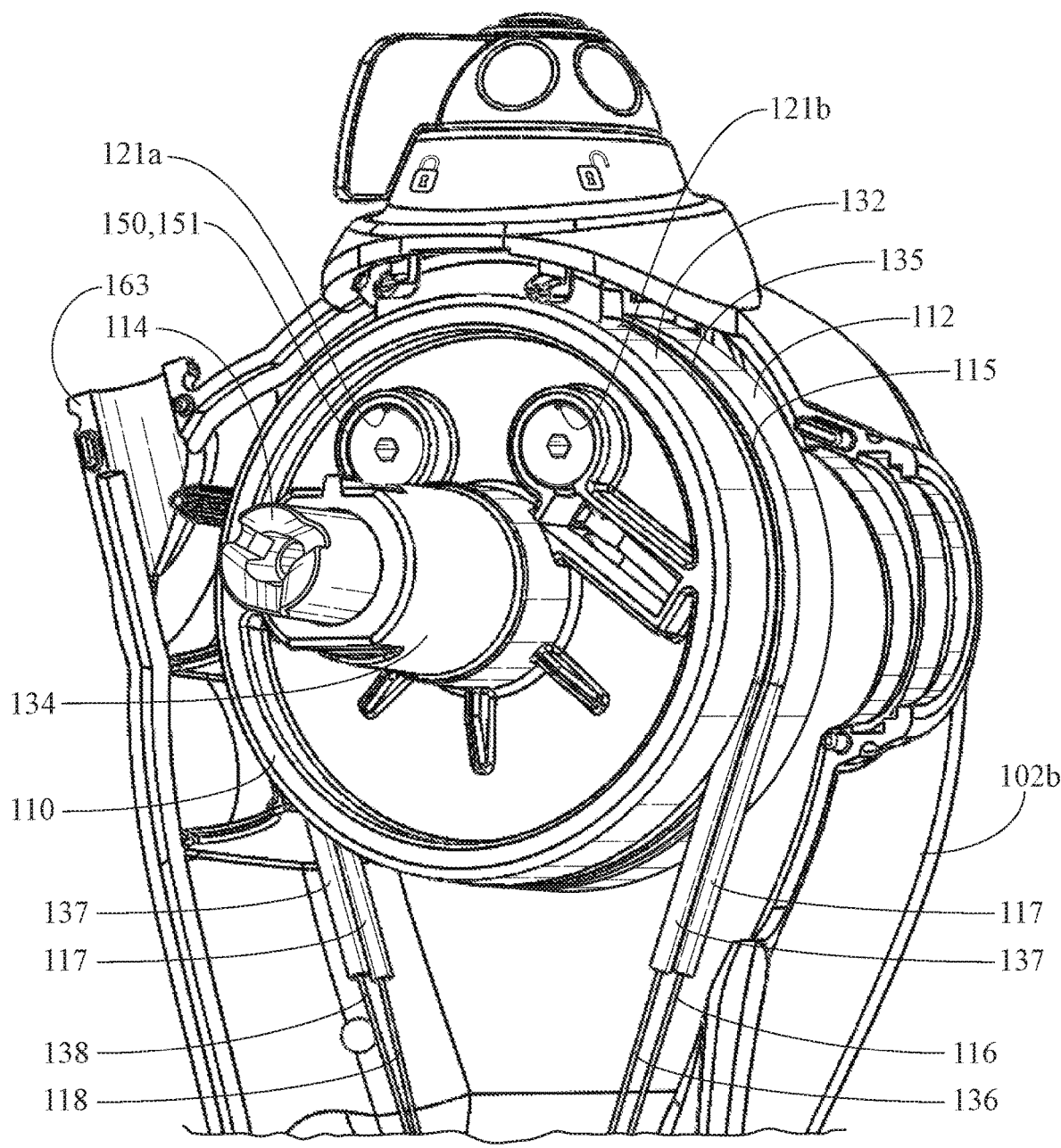
FIG. 3 is a partially disassembled perspective view of the device embodiment of FIG. 2.

The partially disassembled view of the control handle portion of the steerable catheter device 100 shown in FIG. 3 depicts a portion 102b of the handle body 102, with the outer control wheel 110, and the inner control wheel 130 removed, so that the spool assemblies are shown in more detail. The outer control wheel 110 engages a shaft 114 of, and controls rotation of, an outer spool 112 around a common central rotational axis (that preferably is orthogonal to the generally circular handle and spool). The outer spool 112 includes a circumferential groove 115 around its outer circumferential surface, which groove 115 receives a tube 117 through which extend the proximal end regions of opposed first and second control fibers 116, 118. The outer spool 112 includes two gear-mounting apertures 121a, 121b, each of which receives and forms a rotation-permitting engagement with the split mounting end 152 of a gear 150. Each spool includes at least one face surface intersecting the spool axis (preferably having the major face congruent with a plane that is orthogonal to that spool rotational axis).

The inner control wheel 130 engages a shaft 134 of, and controls rotation of, an inner spool 132. The inner spool 132 includes a circumferential groove 135 around its outer circumferential surface, which groove 135 receives a tube 137 through which extend the proximal end regions of opposed third and fourth control fibers 136, 138. The proximal end terminus of each control wire (not shown) is secured to its respective spool. Those of skill in the art will appreciate that rotary actuation of the outer control wheel 110 effects corresponding rotary actuation of the outer spool 112, while rotary actuation of the inner control wheel 130 effects corresponding rotary actuation of the outer spool 132, and that respective distal attachments of each control fiber to/in the distal end lengthwise portion 160 of the catheter body 104 will provide for controllable deflection. As will be understood with reference to FIGS. 2 and 3, the outer spool shaft 114 extends through and beyond a central passage of the inner spool 132 and its shaft 134.

Shaft construction embodiments are described here with particular reference for FIG. 4, which shows a longitudinal section view of the entire shaft, rendered in simplified and partially-exploded diagrammatic fashion, which is not to scale, and which does not include illustration of the catheter's longitudinal lumens. Further construction details of the catheter shaft embodiments may be understood with reference to FIG. 5, which shows a transverse section view of the catheter body 104 (taken along line 5-5 of FIG. 2).

The catheter body 104 shown includes eight lumens that extend longitudinally from a proximal end within the handle 102 through all or nearly all (that is, at least a majority) of the catheter body's entire length, where some or all of those lumens are at least generally, preferably substantially, or even exactly parallel with each other and with a longitudinal center axis of the body, to the distal terminus of the distal end length portion 160. Some embodiments may include fewer than eight lumens, but most preferably include at least two wire control lumens that will provide for steering/deflection along at least one plane by actuation of control fibers therethrough, and preferably having identical or nearly identical inner diameters. The first and second control wire lumens 166, 168 may receive the paired opposite control wires 116, 118, where the first and second lumens are disposed radially 180° opposite each other across a radially off-center longitudinal axis of the catheter body. If present, third and fourth control wire lumens 176, 178 may receive the paired opposite control wires 136, 138, where the third and fourth lumens also are disposed radially 180° opposite each other across a radially off-center longitudinal axis of the catheter body; in other embodiments that intersection may occur across the radially centered longitudinal axis of the catheter body 104. As shown, relative to the radially off-center longitudinal axis of the catheter body, the first and fourth lumens, and the second and third lumens each are disposed radially less than 90° from each other, respectively. Other, larger lumens shown may be configured for purposes other than allowing passage of a control wire (e.g., for passage of a wire guide or other accessory, illumination structure, visualization elements/structures, introduction/extraction of fluids, and/or other purposes). In one embodiment, the outer diameter of the catheter shaft 104 may be about 3.5 to about 4 mm, with the inner diameter of the control wire lumens 166, 168, 176, 178 each being about 0.3 mm, and the inner diameters of the other lumens ranging from about 0.75 mm to about 1.5 mm. In certain embodiments, at least the four wire lumens will have the same diameter, which is one half or less of the largest diameter lumen, and which may be only one fifth of the largest diameter lumen. Intermediate sized lumens may have about two to two and a half the inner diameter of the wire lumens, and may have about one have the inner diameter of the largest lumen.

Figure 5:
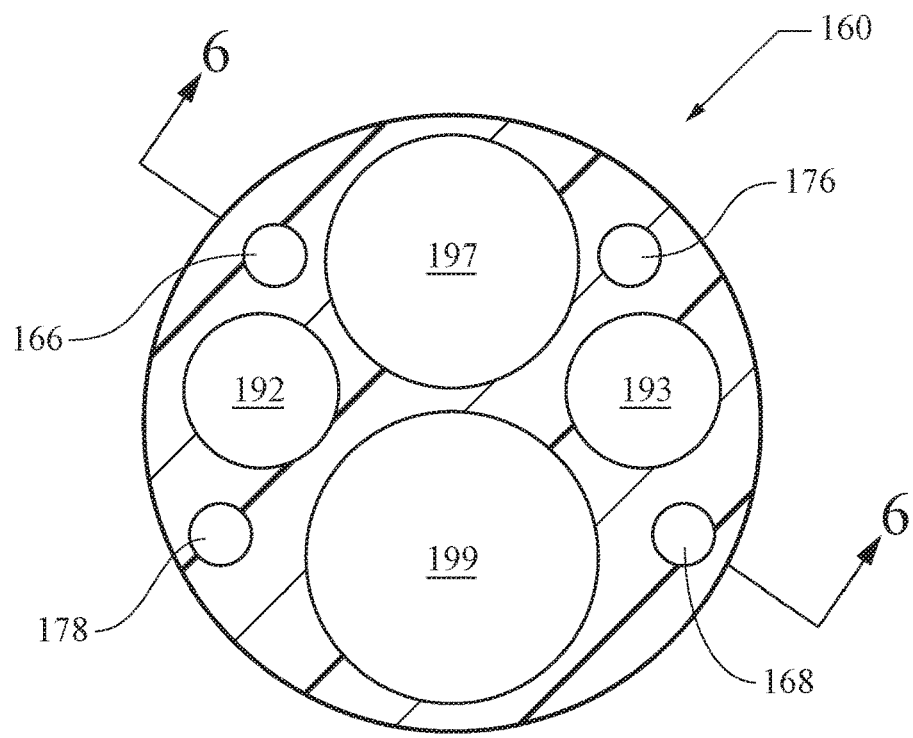
FIG. 5 is a transverse section view taken along line 5-5 of FIG. 2, showing an eight-lumen catheter body.

For example, as shown in FIG. 5, a largest lumen 199 may be useful as a primary working lumen or accessory channel useful for passage of endoscopic tools (e.g., biopsy forceps, needle knife, therapeutic and/or biopsy needle, etc.). In some embodiments this working lumen 199 may have an inner diameter of about 1.5 mm. A second-largest lumen 197, parallel with the other lumens, may be used for other devices such as, for example, a camera or other visualization device which may be removably or permanently disposed in that second-largest lumen 197. In some embodiments this second-largest lumen 199 may have an inner diameter of about 1.3 mm. A pair of opposed side lumens 192, 193, parallel with the other lumens, may be disposed adjacent the larger lumens 197, 199 and—respectively—between the control wire lumens. In some embodiments these side lumens 192, 193 may each have an inner diameter of about 0.75 mm, which may be useful for a variety of functions (for example, passage of small devices such as wire guide(s), light fiber(s), and/or of fluid—e.g., flush fluid, radio-opaque contrast fluid, dyes). One or more of the lumens may also be placed in fluid communication with a vacuum source. As rendered, FIG. 5 is at least generally "to scale" with regard to the relative dimensions of the body and lumens, and—for certain embodiments—will be exactly to scale.

Figure 6:
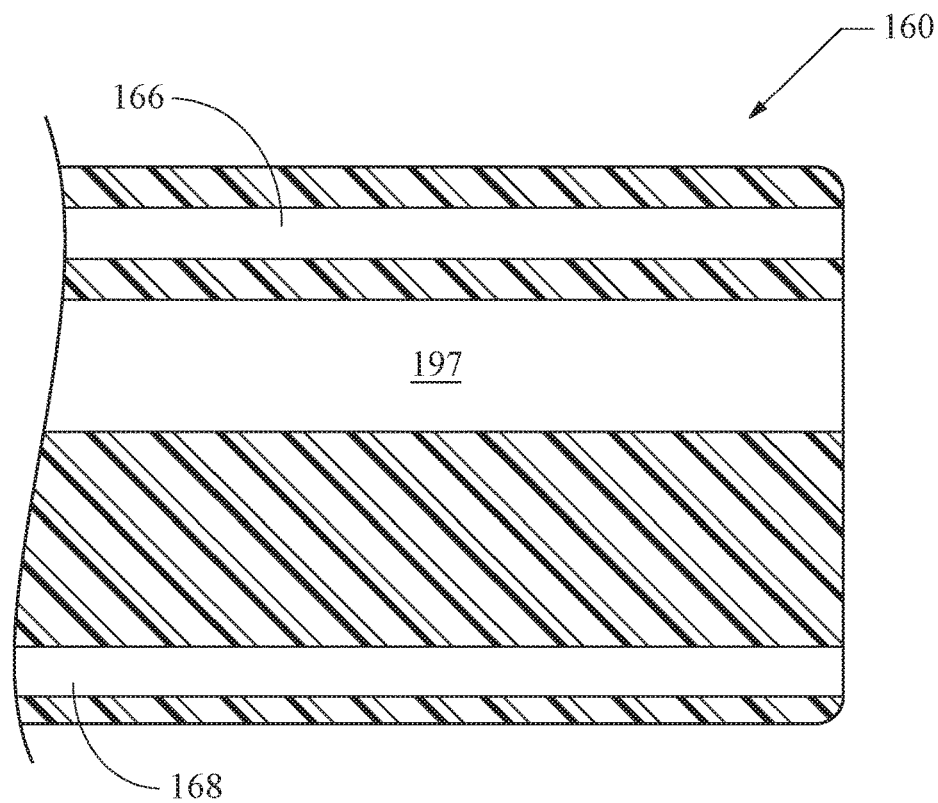
FIG. 6 is a magnified (not-to-scale) longitudinal section view of the distal terminal end portion of the catheter body, taken along line 6-6 of FIG. 5.

Within each of the control wire lumens, the respective control wire most preferably is free to move longitudinally except for a distalmost length that is securely and fixedly attached within a distalmost terminal length of the corresponding control wire lumen. In some embodiments, at least that a distalmost terminal length of the control wire lumen has a consistent/constant and uniform inner diameter that expressly does not get larger at or near the distalmost terminus of the catheter body. In other embodiments, the distalmost terminal length of the control wire lumen may be slightly but smoothly flared to a larger inner diameter, but without any stepped or sharp transition of diameter. The distal end lumen structure is also clearly shown in FIG. 6, which is a longitudinal section view of the distal catheter body portion 160 taken along line 6-6 of FIG. 5, crossing through the radially off-center longitudinal axis.

Embodiments of a steerable or otherwise deflectable catheter body 104 preferably will include different flexibility properties along the length of that body. In particular, a small-diameter body configured for use as a steerable catheter equipped as a cholangioscope that is dimensioned for navigation through a working channel of a larger endoscope and for operation within the biliary tree of a human patient may include properties and construction details as set forth herein. By "small diameter," this catheter shaft disclosure refers to a size of about 10.5 Fr (about 3.5 mm outer diameter), and including outer diameter potential size range of about 2.5 mm to about 5 mm. FIG. 4A shows a diagrammatic, more-assembled view of the catheter body 104 of FIG. 4, which also is not to scale and does not show the lumens, while FIG. 4B depicts a transverse section view thereof taken along line 4B-4B of FIG. 4A where the lumens and main body are generally proportional to each other, but the outer layer is magnified and therefore not proportional.

As shown in FIG. 4, a proximalmost shaft length 1104 may be constructed as an extruded, machined, or otherwise-formed tube with a harder stiffness, where the tube length here is a multilumen tube (preferably of the construction shown in FIG. 4, but not limited to such unless expressly qualified). In quantitative terms, the tube forming this proximalmost shaft length 1104 may be formed of a polymer or mix of polymers providing the desired stiffness (e.g., one or more of a polyether block amide, such as PEBAX™ polymers, nylon, and/or other polymer(s) known or developed and suitable for use in medical devices, where the exemplary materials disclosed here are not limiting or exclusive unless expressly stated to be so). The stiffness/flexibility relates to the hardness of material(s) used, which may be in range of about 66 D to about 80 D (Shore D hardness measure of durometer). In one example, the proximalmost shaft length 1104 is extruded as a blend of 72 D PEBAX™ and Nylon-12, proportioned within the blend to provide a Shore D hardness of about 77 D. For use in a cholangioscope having a total shaft length (including an intra-handle-body length) of about 200 cm to about 230 cm, the proximalmost shaft length 1104 may be about 185 cm to about 105 cm in length, with one embodiment constructed as being 196.5 cm in length. These lengths can readily be increased or decreased depending upon the operating environment in which the catheter is going to be used (e.g., different sized "parent" scopes through which it may be operated). The polymer blend may include equal or unequal parts of one, two, three, or more polymers, selected to provide the desired stiffness/flexibility as known to those of skill in the arts of polymers, tube manufacture, and medical device manufacture. For each of construction elements where hardness/durometer is described, the durometer given is that of the materials used and should not be interpreted as a durometric test or data for the catheter shaft or other structure as constructed.

The shaft composition described is sufficiently flexible to be navigated readily into and through a working channel of a larger endoscope (e.g., as shown in FIGS. 1, 1A, 1B), while providing sufficient stiffness/rigidity to limit columnar and radial compression while operating the steering/deflection mechanism in a manner that predictably and accurately will deflect the distalmost end length 160 of the overall shaft 104. Unless otherwise specified, the general properties and variances described for the composition and construction of this proximalmost shaft length 1104 apply to the other shaft lengths described elsewhere herein. In the illustrated embodiment, the proximalmost shaft length 1104 does not include any additional internal or external reinforcement structures attached thereto or embedded therein for a majority of its length, or even for its entire length.

In an assembled catheter body 104, the proximalmost shaft length 1104 may be fixedly joined to a proximal intermediate shaft length 1204, which may be constructed as an extruded, machined, or otherwise-formed tube with a moderate stiffness. The joining may be done by thermal bonding to form a secure and permanent butt joint weld, by adhesive, or by other means for forming a secure and permanent joint between the segments 1104, 1204. One or more of the same (or different) joining means may be used to connect each of the segments of the catheter body 104. The tube forming this proximalmost shaft length 1204 may be formed of a polymer or mix of polymers providing the desired stiffness (e.g., one or more of a polyether block amide, such as a PEBAX™ polymers, nylon, and/or other polymer(s) known or developed and suitable for use in medical devices).

The moderate stiffness of this proximal intermediate shaft length 1204 relates to the hardness of material(s) used, which may be in range of about 50 D to about 65 D. In one example, the proximal intermediate shaft length 1204 is extruded as a 63 D PEBAX™ tube. For use in a cholangioscope having a total shaft length (including an intra-handle-body length) of about 200 cm to about 230 cm, this shaft length 1204 may be about 15 cm to about 30 cm in length, with one embodiment constructed as being 21 cm in length. These lengths can readily be increased or decreased depending upon the operating environment in which the catheter is going to be used (e.g., different sized "parent" scopes through which it may be operated). This length may be considered as an "elevator section," which is constructed with greater flexibility than the proximalmost length 1104 and the distalmost length 1404. This flexibility provides for ease of manipulation across and with an elevator of a duodenoscope without kinking or crimping.

To further aid its elevator section structure and function, this proximal intermediate shaft length 1204 is shown as being circumferentially reinforced with a metallic or polymeric coil 1205 that tightly conforms around the outer diameter surface of the proximal intermediate shaft length 1204. The coil 1205 may include a flat cross section across its body and be configured as a helix that is set at a pitch of about 34 coils per inch (about 13.4 coils per cm). By "flat cross section across its body," it is meant that—as shown in FIG. 4—a longitudinal/sagittal section view will show the cross-section as being generally rectangular (including obround, elliptical). However, it should be appreciated that the coil construction, including its pitch, may be changed to increase or decrease the flexibility of this proximal intermediate shaft length 1204. One exemplary coil is metallic, 0.012 inches (about 0.3 mm) wide across its body, and 0.002 inches thick (about 0.05 mm), with a pitch of 34 coils per inch. The proximal end of the coil 1205 may be disposed near, at, or slightly overlapping with the joint of the proximal intermediate shaft length 1204 with the proximalmost length 1104. The coil 1205 prevents, or at least significantly reduces likelihood of, radial compression of the lumens when the catheter shaft 104 is being operated across a duodenoscope elevator and/or within tortuous body lumens or passages (e.g., lumens of the biliary tree of a human or animal patient such as during a cholangioscopy procedure).

In the embodiments disclosed here, a coil is preferred to a braid or braid-like reinforcement structure for several reasons including that a coil as provided provides better resistance to compression/crushing of the catheter lumens while maintaining a small radial profile and supporting non-kinking tight curvature (e.g., across a duodenoscope elevator), and a coil reduces material and manufacturing costs (which helps to save money for patients, hospitals, and insurers). The single-layer flat coil of the present embodiments may be a 304 stainless steel coil of a type known in the art (e.g., as used in various Flexor® products available from Cook, Inc. of Bloomington, Ind.). With the very small dimensions of the present embodiments, the coil's combination of strength and flexibility and strength (with particular regard to resisting radial compression) is superior to that of a braid, where the braid must include overlapping wires and must have special end-terminal construction to secure the wire ends. As such, a braid may be useful in certain embodiments of a catheter body disclosed here, but generally be less preferred.

As illustrated in FIG. 4, in the catheter body 104, the proximal intermediate shaft length 1204 may be joined to a distal intermediate shaft length 1304 ("deflection section 1304"), which may be constructed as an extruded, machined, or otherwise-formed tube with a softer stiffness that is the softest/most flexible of the entire catheter length. The joining may be done by thermal bonding to form a secure and permanent butt joint weld, by adhesive, or by other means for forming a secure and permanent joint between the segments 1204, 1304. The tube forming this distal intermediate shaft length 1304 may be formed of a polymer or mix of polymers providing the desired stiffness (e.g., one or more of a polyether block amide, such as a PEBAX™ polymer, nylon, and/or other polymer(s) known or developed and suitable for use in medical devices).

The softer stiffness of this distal intermediate shaft length 1304 may be in a hardness range of about 30 D to about 49 D. In one example, the distal intermediate shaft length 1304 is extruded as a PEBAX™ tube (about 42 D, from a blend of 45 D and 35 D PEBAX™ polymers). For use in a cholangioscope having a total shaft length (including an intra-handle-body length) of about 200 cm to about 230 cm, this shaft length 1304 may be about 1.5 cm to about 3 cm in length, with one embodiment constructed as being 2.6 cm in length. These lengths can readily be increased or decreased depending upon the operating environment in which the catheter is going to be used (e.g., different sized "parent" scopes through which it may be operated). The coil 1205 may extend near, to, or across the joint between the proximal intermediate shaft length 1204 and the distal intermediate shaft length 1304, and in some embodiments (not shown but readily understandable by those of skill in the art with reference to the present disclosure), the coil—whether with a same or different pitch and/or coil construction than over the proximal intermediate shaft length 1204—may extend around some or all of the deflecting segment of the distal intermediate shaft length 1304.

The construction of this deflecting section 1304 provides a curving/bending region across which the control wires can bend/deflect the distalmost shaft end including articulation that may be up to 90° relative to the catheter shaft's longitudinal axis, with 360 of radial rotation in certain embodiments. The particular steering mechanism may use control wires as described above, or any other steering or deflection mechanism known or developed. In embodiments with a coil and/or other reinforcement around this section 1304, the flexibility and steering responsiveness may decrease while the robustness of the catheter increases.

As shown in FIGS. 4, 4A, and 4B, an outer reflow layer 1505 may also be provided around at least the proximal intermediate shaft length 1204 and the distal intermediate shaft length 1304. The reflow layer 1505 may be provided as a tubular reinforcing sleeve that is placed around a chosen lengthwise region—e.g., upon which the coil has been wound—then "melted"/"reflowed" on using, for example an FEP (fluorinated ethylene propylene) or other heat-shrink oversleeve, which oversleeve is thereafter removed in a technique well-known in the art. This securely and permanently fixes the sleeve as a reflow layer to and around the coil and the underlying catheter shaft lengths. Composition of the reflow layer 1505 may include PEBAX™ and/or other polymers, and formation of the reflow layer in this manner will bind the reflow layer 1505 to the outer surface of the underlying shaft body. It will also conform the reflow layer 1505 through and around the coil 1205 in a manner firmly integrating that coil to the overall catheter body structure. The sizes and tolerances of the coil 1205 and the underlying main tubular catheter body structure can provide a tight fit therebetween such that none of the reflow layer 1505 is disposed therebetween, or there may be some gap/tolerance such that at least some portion of the reflow layer 1505 is between the coil and the underlying catheter tube body.

In the embodiment illustrated in FIGS. 4-4A, the reflow layer 1505 includes a proximal reflow length 1505a and a distal reflow length 1505b. The proximal reflow length 1505a is formed from a stiffer (greater durometer) polymer such as, for example a PEBAX™ that may have the same or nearly the same Shore D hardness as the proximal intermediate shaft length 1204 (e.g., within +/−5 D). So, for example, in an embodiment where the proximal intermediate shaft length 1204 is formed from a 63 D polymer, the proximal reflow length 1505a may be formed from a 61 D, 62 D, 63 D, 64 D, or 65 D polymer. The distal reflow length 1505b is formed from a softer (lower durometer) polymer such as, for example a PEBAX™ that may have the same or nearly the same Shore D hardness as the distal intermediate shaft length 1304. So, for example, in an embodiment where the proximal distal shaft length 1204 is formed from a 42 D polymer, the distal reflow length 1505b may be formed from a 45 D polymer, where certain embodiments will include a distal reflow length that is stiffer than the underlying soft deflection segment 1304.

This reflow layer 1505 may be an extruded tube (or tubes) that, when assembled to the overall catheter device, will help to resist crimping and/or kinking as well as damage from an endoscope elevator during a procedure using the device. It may extend from proximal of the joint between the proximalmost shaft length 1104 and the proximal intermediate shaft length 1204 to distal of the joint between the distal intermediate shaft length 1304 and the distalmost shaft length 1404. The two different-stiffness regions 1505a, 1505b overlying the catheter body provide a transition zone for overall device flexibility that provides robust support resisting crimping and/or kinking while providing responsive deflection/steering behavior during operation. Unlike the stepped transition between the reflow layer in the outer catheter body surface shown in the diagrammatic, not-to-scale illustrations of FIGS. 4-4A, physical embodiments will have a smooth transition that may be nearly visually imperceptible without high magnification (particularly for embodiments where the overall device outer diameter is no more than about 3.5 mm and the reflow layer with coil is only about 0.004 inches thick or less (about 0.1 mm or less).

The entire reflow layer 1505 preferably is extruded as a single-layer tube that (before being heat-shrunk/reflowed) is oversized to fit around the outer diameter of the catheter body 104 and coil 1205. Its initial dimensions may include an inner diameter of about 0.135 inches (about 3.43 mm) and a wall thickness of about 0.0035 inches to about 0.0055 inches (about 0.089 mm to about 0.014 mm). In one embodiment, the overall sleeve of the reflow layer 1505 may be about 27 cm long (+/−3 cm) and extend from a distal end at the joint between the distal intermediate shaft length 1304 and the distalmost shaft length 1404 to proximal of the joint between proximalmost shaft length 1104 and the proximal intermediate shaft length 1204. In one such non-limiting embodiment the proximal/stiffer reflow length 1505a may be about 22 cm long, and the distal/softer reflow length 1505b may be about 5.3 cm long.

During assembly of the sleeve(s) for the reflow layer 1505 to the underlying catheter body 104, the catheter lumens may be kept open and patent by PTFE-coated stainless steel/nitinol mandrels. In one such method, the mandrels used may have diameters of (and thereby provide for catheter lumen diameters of) about 0.0115 inches, 0.0315 inches, 0.05 inches, and 0.06 inches (about 0.292 mm, 0.8 mm, 1.3 mm, and 1.5 mm, respectively). The maximum overall diameter—including the reflow layer 1505, coil 1205, and catheter body/core preferably is about 10.5 Fr or less.

The distalmost segment of shaft length 1404 may be joined with the thermowelded butt joint or other means to the distal end of the distal intermediate shaft length 1304. The tube forming this distalmost shaft length 1404 may be formed of a polymer or mix of polymers providing the desired stiffness (e.g., one or more of a polyether block amide, such as a PEBAX™ polymer, nylon, and/or other polymer(s) known or developed and suitable for use in medical devices). This distal terminal end segment of the catheter body 104 will be stiffer than the deflection segment 1304.

The greater stiffness of this distalmost shaft length 1404 may be in the same or nearly the same hardness range as the unreinforced proximalmost shaft length 1104. Its length preferably is as short as possible to provide a stiffer distal end length that will provide for securely and permanently anchoring distalmost ends of control wires and also will permanently anchor to the distal intermediate shaft length 1304. The composition of this distalmost shaft length 1404 may be the same as or nearly the same as the proximalmost shaft length 1104. The hardness of material(s) used, may be in range of about 66 D to about 80 D. In one example, the distalmost shaft length 1404 is extruded as a blend of 72 D PEBAX™ and Nylon-12, proportioned within the blend to provide a hardness of about 77 D. For use in a cholangioscope having a total shaft length (including an intra-handle-body length) of about 200 cm to about 230 cm, this shaft length 1404 may be about less than 1 cm, with one embodiment constructed as being 0.4 cm in length. These lengths can readily be increased or decreased depending upon the operating environment in which the catheter is going to be used (e.g., different sized "parent" scopes through which it may be operated, and the specific desired performance environment for the distal end of the overall device).

Certain advantages in controlling costs for patients and physicians can be realized in the presently disclosed embodiments. For example, certain prior steerable catheters include lumen liner material in one or more lumens; although such may be useful and may readily be implemented with catheter shafts of this disclosure, it is preferable not to include lumen liner material. Certain prior steerable catheters include a braided reinforcement sleeve along at least one length (e.g., encompassing or embedded in the catheter wall); although such may be useful and may readily be implemented with catheter shafts of this disclosure, it is preferable not to include a braided sleeve but rather to implement one or more of the coil and reflow layer described herein.

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment. In the event of any inconsistent disclosure or definition from the present application conflicting with any document incorporated by reference, the disclosure or definition herein shall be deemed to prevail.

We claim:

1. A steerable catheter device, comprising:
    a multilumen catheter shaft body, which catheter shaft body comprises:
        a proximal end length having a first durometer;
        a proximal intermediate length fixedly joined to a distal end of the proximal end length and having a second durometer;
        a distal intermediate length fixedly joined to a distal end of the proximal intermediate length and having a third durometer; and
        a distal terminal end length fixedly joined to a distal end of the distal intermediate length and having a fourth durometer;
    where the proximal end length is the longest of the lengths and has a higher durometer than at least the proximal intermediate length and the distal intermediate length;
    where the distal terminal end length is the shortest of the lengths and has a higher durometer than at least the proximal intermediate length and the distal intermediate length;
    a tubular sleeve disposed around at least the proximal intermediate length and the distal intermediate length, the tubular sleeve including a first sleeve durometer of a first lengthwise portion of the tubular sleeve and a second sleeve durometer of a second lengthwise portion of the tubular sleeve distal of the first lengthwise portion, with a proximal end of the tubular sleeve being nearer to a distal terminal end of the catheter shaft body than to a proximal terminal end of the catheter shaft body; and
    where a plurality of longitudinal lumens extends through at least a majority length of the catheter shaft body.

2. The catheter device of claim 1, where at least some of the plurality of longitudinal lumens are parallel with each other and with a longitudinal center axis of the catheter shaft body, and where a visualization device is disposed in one of the plurality of longitudinal lumens.

3. The catheter device of claim 1, where the plurality of longitudinal lumens includes eight lumens.

4. The catheter device of claim 1, where the plurality of longitudinal lumens includes four steering control wire lumens parallel with each other and with a longitudinal center axis of the catheter shaft body, which steering control wire lumens have smaller inner diameters than any other lumens of the catheter shaft body.

5. The catheter device of claim 1, where the first durometer and the fourth durometer are the same.

6. The catheter device of claim 1, where the first durometer, the second durometer, and the fourth durometer each is greater than the third durometer.

7. The catheter device of claim 1, further comprising a coil disposed around an outer circumferential surface of the catheter shaft body along at least the proximal intermediate length.

8. The catheter device of claim 7, wherein the tubular sleeve is embodied as a reflow layer and is disposed around at least the coil, and where a proximal end of the coil is disposed near, at, or slightly overlapping with a joint of the proximal intermediate length with the proximal end length.

9. The catheter device of claim 8, where the tubular sleeve is securely fixed to and around a chosen lengthwise region occupied by the coil, and where a portion of the tubular sleeve is disposed radially between the coil and the catheter shaft body.

10. The catheter device of claim 1, where the first sleeve durometer, overlying at least part of the proximal intermediate length, is greater than the second sleeve durometer, overlying at least part of the distal intermediate length.

11. The catheter device of claim 10, where the first lengthwise portion of the tubular sleeve overlaps a joint between the proximal end length and the proximal intermediate length, and the second lengthwise portion of the tubular sleeve overlaps a joint between the proximal intermediate length and the distal intermediate length.

12. The catheter device of claim 10, where the second lengthwise portion of the tubular sleeve also overlaps a joint between the distal intermediate length and the distal terminal end length.

13. The catheter device of claim 10, where the first sleeve durometer is the same as the durometer of the proximal intermediate length.

14. The catheter device of claim 10, where the second sleeve durometer is the same as the durometer of the distal intermediate length.

15. The catheter device of claim 1, where an outer diameter of the catheter shaft body does not exceed 10.5 French.

16. The catheter device of claim 1, further comprising at least one control wire disposed longitudinally through at least one of the lumens.

17. The catheter device of claim 1, further comprising a plurality of control wires disposed longitudinally, with at least one of the control wires disposed through each of at least two of the lumens, where at least one of the plurality of control wires comprises an optical fiber.

18. The catheter device of claim 1, where a smallest lumen of the plurality of longitudinal lumens has an inner diameter between one fifth and one half the inner diameter of a largest lumen of the plurality of longitudinal lumens.

* * * * *